United States Patent [19]

Cronk et al.

[11] Patent Number: 4,572,170
[45] Date of Patent: Feb. 25, 1986

[54] PREVENTIVE KNEE BRACE

[76] Inventors: Richard V. Cronk, 1175 NW. Overlook Dr.; Jean-Paul Nielsen, 445 NW. Eighth ST., both of Corvallis, Oreg. 97330

[21] Appl. No.: 617,693

[22] Filed: Jun. 6, 1984

[51] Int. Cl.$^4$ ............................................. A61F 3/00
[52] U.S. Cl. ................................... 128/80 C; 128/88
[58] Field of Search ................ 128/80 C, 80 F, 80 R, 128/88, 87 R, 83, 165; 3/22

[56] References Cited

U.S. PATENT DOCUMENTS 4,249,524  2/1981  Anderson ......................... 128/80 C Primary Examiner—Jay N. Eskovitz
Attorney, Agent, or Firm—Klarquist, Sparkman, Campbell, Leigh & Whinston

[57] ABSTRACT

A preventive single-sided knee brace for athletes includes independently pivotable and laterally rigid upper and lower leg bars interconnected at laterally rigid polycentric clevis joints of a shield plate assembly. Straps affixed to a knee plate of the shield plate assembly encircle the leg adjacent the knee joint and buckle to the knee plate to hold the assembly adjacent the lateral side of the knee joint in any position of leg flexion. The upper leg bar extends from the shield plate assembly along the outside of the upper leg and is secured to the leg at the bar's upper end. Similarly, the lower leg bar extends from the polycentric joint along the outside of the lower leg and is secured to the leg at the bar's lower end. The upper and lower leg bars are shaped to follow the contour of the leg and bridge the knee joint to hold the shield plate assembly laterally spaced from the side of the knee joint.

16 Claims, 4 Drawing Figures

PREVENTIVE KNEE BRACE

BACKGROUND OF THE INVENTION

This invention relates to an improved preventive knee brace. More particularly, this invention relates to an improved single-sided preventive brace for use by athletes to protect the knee joint against damage from lateral impact.

The knee joint is composed of three separate bones and associated ligaments binding them together. At the joint, the lower end of the femur meets the upper end of the tibia. The kneecap, or patella, lies across the front of the joint. On the lateral and medial sides of the adjacent ends of the femur and tibia are a pair of knuckle-shaped protrusions, or condyles. The condyles of the femur rest upon the adjacent condyles of the tibia, which provide a wide base of support for the joint. The condyles also serve as points of attachment for the associated ligaments and muscles which bind the bones together to form the joint.

These bones and ligaments form a complex, hinge-type joint which restricts movement of the lower leg to a single plane. In operation, the joint involves gliding, rolling, and rotational movements which cause it to shift forward during extension of the lower leg and backward during flexion. This shifting results from the interaction of the uneven adjacent condyle surfaces.

Because of its limited planar movement, the knee joint is peculiarly susceptible to damage. Injury to the joint is caused in many cases by sudden movement to the side, such as a quick change of direction in running, or by a lateral blow to the joint. With the foot planted, the tibia is relatively fixed. A sideways blow to the femur may cause it to move laterally relative to the tibia, tearing the associated ligaments and upper leg muscles from the joint. A blow to the tibia when the foot is raised may cause similar damage to the lower leg.

Knee braces fall into two general functional categories, rehabilitative and preventive. Both typically comprise a pair of elongated support bars extending along one or both sides of the leg and hinged at the knee joint.

Rehabilitative braces use the support bars and connecting hinge, often in conjunction with a cast, to relieve stress on a weakened joint. A rehabilitative brace also deliberately limits the normal flexion and extension of the leg and prevents sideways movement of the joint. With the joint's movement limited, the muscles and ligaments can reattach to the bones and heal internal tears. Many rehabilitative braces permit the leg's range of motion to be gradually increased so that the user can strengthen the ligaments and muscles by moving and working them. Rehabilitative braces are usually heavy and cumbersome and restrict mobility. Therefore, they are unsuitable for use by athletes who need maximum freedom of leg motion.

In contrast, preventive knee braces are worn by athletes solely to prevent an injury. They are designed to protect the knee by preventing sideways movement of the femur relative to the tibia without hindering the normal flexion or extension of the leg. This sideways movement can occur either from internal stress on the joint caused by a rapid change in direction during fast movement or from external stress caused by a lateral blow to the knee joint from a block or tackle. Ideally, to provide the necessary protection without interfering with the user's mobility, preventive braces should be strong, laterally rigid, lightweight, and not cumbersome. They should also shield the knee from lateral blows in all positions of leg flexion. Heretofore, preventive braces have not fulfilled all of these objectives.

U.S. Pat. No. 4,337,764 to Lerman discloses the principal drawbacks of a rehabilitative brace. The brace has a pair of bars extending along one side of the leg and pivotally connected outside the knee joint at a plate assembly defining a polycentric clevis joint. The bars are embedded in a plaster cast to rigidify the bars and provide support at the knee joint for limited movement of the leg while in the cast. The adjacent ends of the bars meeting at the joint have intermeshing teeth to force both bars to pivot interdependently, allowing the user to use the muscles of his upper leg, for example, to extend or flex the lower leg or vice versa. Adjustable stops on the plate assembly further limit the maximum angular movement of the leg in flexion or extension. Such limitations on joint motion may aid in healing torn ligaments but render the brace unacceptable for active wear. The interdependent and limited movement of the bars in conjunction with the heavy, cumbersome plaster casts would obviously and severely inhibit mobility.

Other rehabilitative braces suffer from similar limitations on mobility. U.S. Pat. No. 4,372,298 to Lerman discloses a cumbersome, double-sided brace with U-shaped upper and lower yoke-like support members fitting around the back of the leg. Upper and lower bars interconnecting the support members at opposite sides of the leg pivot interdependently at a pair of polycentric clevis joints within massive knee plate assemblies to limit free movement of the knee joint. Flexion of the leg in particular is curtailed by the close fitting and firmly attached support members. U.S. Pat. No. 4,361,142 to Lewis et al. and Canadian Patent No. 1,011,204 to Patel also feature supportive but cumbersome, motion-inhibiting double-sided bracing similar to that of the brace of Lerman —298, and have many of the same limitations. U.S. Pat. No. 4,340,041 to Frank discloses a knee splint with long, thin upper and lower leg bars embedded in plaster casts and joined to each other at a single-pivoting joint connection. The connection is adjustably set to hold the leg member at a selected angle to promote proper healing of the knee joint. However, the set splint prevents any flexion of the leg.

Several of the rehabilitative braces, such as those of Patel and Lerman '298, are also suggested for use as preventive braces. Their double-sided bracing and laterally rigid clevis joints provide limited protection against sideways joint displacement from a severe lateral blow to the knee, but their massive structure and necessarily heavy weight limit free movement of the leg and would induce fatigue. Moreover, their complexity makes them difficult to mount properly to the leg.

Braces designed solely for prevention of athletic injury, on the other hand, typically have single-sided bracing to reduce bulk and weight, and to permit greater freedom of leg movement. The single-sided bracing extends along one side of the leg to prevent sideways movement of the joint caused by sudden changes in running direction. For example, U.S. Pat. No. 4,249,524 to Anderson discloses a single-sided preventive brace having a long and narrow support bar positioned alongside the knee joint. Short, padded plates extending along the upper and lower leg are pivoted at lap joints to each end of the bar. The support bar provides a double-hinged connection between the upper and lower leg which tends to keep them laterally aligned. However, the Anderson brace does not adequately shield the knee joint from a lateral blow in all leg positions. When the leg is flexed, the narrow bar bridges the upper and lower leg behind the knee, exposing it to lateral impact. Moreover, its lap joints provide a poor shield even when the bar covers the knee joint because they are inherently weak, introducing undesirable lateral flexibility to the brace which can result in the transfer of force from a severe lateral blow through the bar directly to the knee.

U.S. Pat. No. 3,528,412 to McDavid discloses another single-sided preventive brace. Its long, thin upper and lower leg members are pivotally interconnected at a single lap joint in the general area of the knee. Its single pivot cannot accurately mimic the complex motion of the knee, thereby leaving the knee unprotected and thus vulnerable to lateral impacts when the leg is flexed. Because of its laterally weak lap joint and thin leg members, the McDavid brace is quite flexible laterally and therefore does not protect the knee from the force of severe lateral blows even when its joint coincides with the knee joint.

A further drawback of existing preventive knee braces is that they are difficult to repair and must usually be returned to the manufacturer for this purpose. This is not only time-consuming but also requires each user to keep a spare one of these custom-fitted braces on hand, effectively doubling their cost.

Accordingly, a need remains for a one-sided preventive knee brace that is lightweight, strong and laterally rigid, and yet effectively shields the knee joint throughout its full range of motion without hindering normal leg movement. There is also a need for such a brace that is quickly and easily repairable by the user or his athletic staff. These are the primary objectives of the present invention.

SUMMARY OF THE INVENTION

The foregoing objectives are carried out by the present invention which comprises a single-sided preventive knee brace having independently pivotable and laterally rigid upper and lower leg bars interconnected at laterally rigid polycentric clevis joints that shield the knee joint against lateral impact in all positions of leg flexion.

Securement means affixed to a shield plate assembly which includes the clevis joints encircles the leg closely adjacent the knee joint for holding the shield plate assembly in position adjacent the lateral side of the knee in all positions of leg flexion. Adjacent ends of the upper and lower bars pivot independently within the assembly to allow maximum freedom of leg motion. The upper leg bar extends from the assembly along the outside of the upper leg and is secured to the leg at the bar's upper end. Similarly, the lower leg bar extends along the lower leg and is secured to the leg at the bar's lower end. The upper and lower leg bars each include a dogleg portion to follow the contours of the leg and bridge the knee joint to hold the shield assembly laterally spaced from the side of the knee joint. In this position, the shield assembly absorbs lateral impact forces directed at the knee joint and transmits them through the upper and lower leg bars away from the joint. The laterally rigid bracing also prevents sideways movement of the knee joint caused by sudden changes in running direction.

The shield plate assembly includes, in addition to the clevis joints, a thin, somewhat flexible knee plate formed to extend about the outside of the knee. The securement means may comprise a strapping system attached to the knee plate. The strapping system may include an adjustable Y-shaped elastic strap which straddles the knee cap as it encircles the knee joint and buckles to the knee plate. The strap holds the shield assembly in its shielding position.

For the shield plate assembly to accurately follow the motion of the knee joint, preferably the upper and lower pivot axes of the clevis joints are spaced substantially the same distance apart as the lateral centers of the adjacent outer condyles of the tibia and femur. This spacing assures that the shield plate assembly always shields the outside of the knee joint regardless of the joint's position.

To aid in dispersing impact forces on the shield plate assembly, the length of each leg bar may be greater than the distance between pivot axes. Such forces are thus transmitted through the leg bars and dissipated over large areas of the upper and lower leg to avoid injury to any portion of the leg.

To facilitate positioning of the bars along the outside of the leg, broad thin, somewhat flexible plates are attached to the free ends of the leg bars. These plates may either be taped or strapped to the leg to hold the leg bars in position. These plates as well as other portions of the brace are easily replaceable by the user because threaded fasteners are used to secure them to their connected parts.

The brace of the present invention is a significant improvement over the prior preventive knee braces. It is strong, laterally rigid and yet of lightweight construction and minimum bulk. It prevents sideways knee joint movement from internal stress and effectively shields the knee joint from lateral impact in all positions of leg flexion without limiting normal leg movements. Its parts can be readily replaced by the user when required.

The foregoing and other objects, features, and advantages of the present invention will become more apparent from the following detailed description which proceeds with reference to the accompanying drawings.

DETAILED DESCRIPTION

Figure 1:
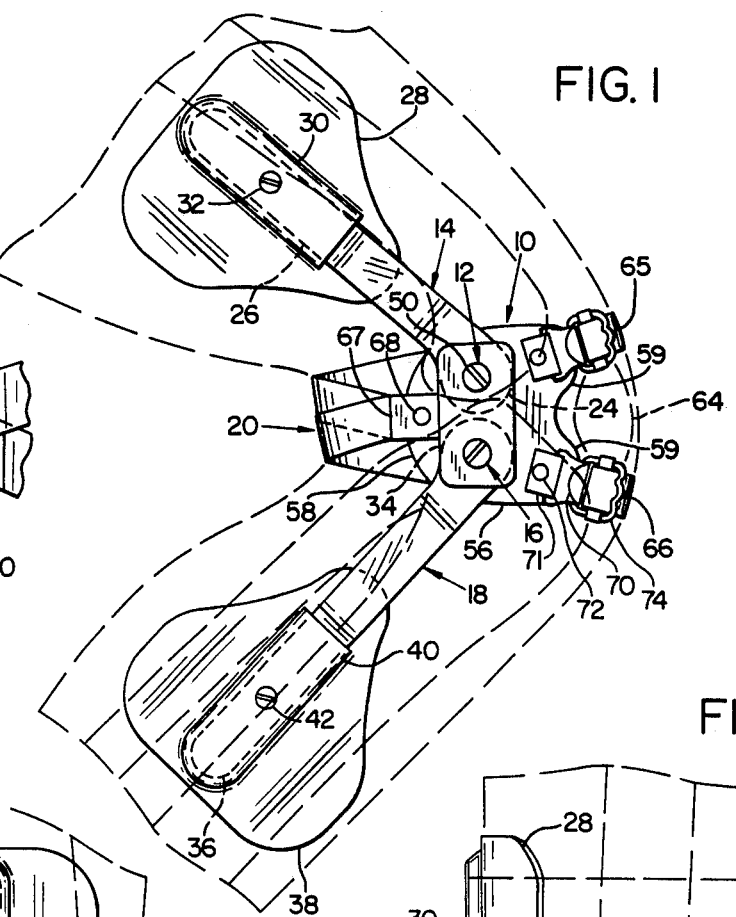
FIG. 1 is a side view showing the knee brace in position on a flexed leg, shown in phantom lines.

Referring to FIG. 1, the knee brace of the present invention includes a shield plate assembly 10 which interconnects an elongated rigid upper leg bar 14 and an elongated rigid lower leg bar 18 at polycentric clevis-type pivot joints 12, 16 for movement independently of one another. Securement means comprising a system of straps 20 hold the shield plate assembly in place alongside the outside of the knee in all positions of leg flexion.

Upper leg bar 14 is preferably of rectangular cross section and composed of stainless steel or a similar lightweight yet strong material. It is typically about one foot in length. A rounded lower portion 24 of the upper bar has an aperture for use in forming part of the upper pivot joint 12. An upper portion 26 of the bar retains a generally triangular shaped upper side or thigh plate 28 of thin, somewhat flexible plastic shaped to fit the curve of the side of the upper leg. The back or outside of plate 28 includes a sleeve 30 extending from an opening at the apex to the midpoint of the base of the plate. The sleeve is sized to slidingly receive bar 14. The plate is removably secured to the bar by a machine screw 32 extending through a midportion of the sleeve into the bar. Leg plate 28 may be secured to the upper leg by attached straps (not shown) or alternatively with tape to hold the leg bar in its desired position along the outside of the upper leg.

Figure 3:
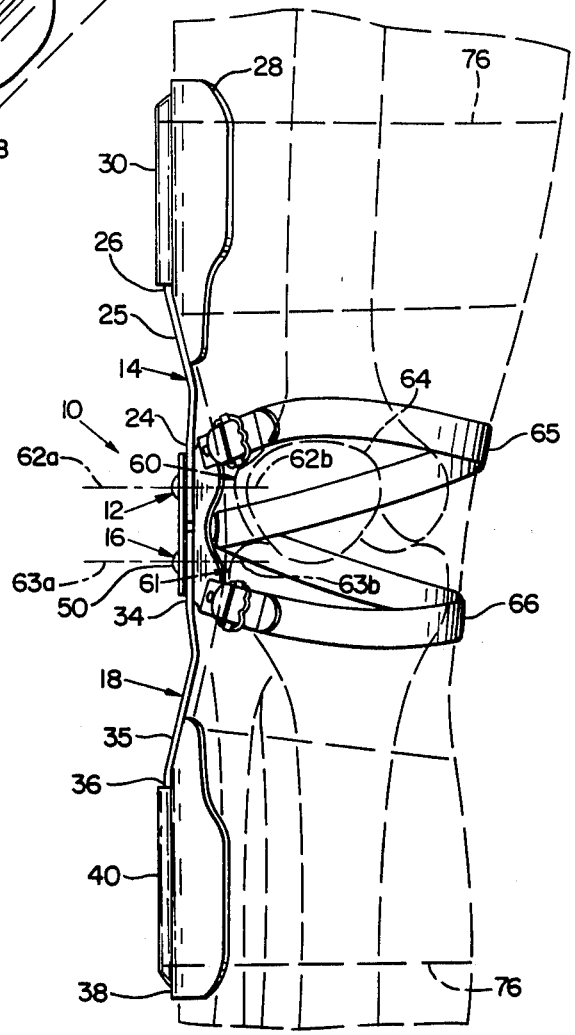
FIG. 3 is an edge view of the knee brace shown in position on an extended leg.

As shown in FIG. 3, upper bar 14 is not straight as viewed edgewise. Upper portion 26 is offset laterally outwardly from lower portion 24 by a dog-leg intermediate bar portion 25, for a purpose to be described below.

The lower leg bar 18 is of similar design and composition as upper bar 14. A rounded upper portion 34 of the lower bar has an aperture forming part of the upper pivot joint 16. A lower portion 36 of bar 18 retains a generally triangular shaped lower side or calf plate 38 of flexible plastic shaped to fit the curve of the lower leg. The outside of plate 38 includes a sleeve 40 extending from an opening at the apex to the midpoint of the base of the plate. The plate and bar are removably secured together by a machine screw 42 extending through a midportion of the sleeve into the bar. Plate 38 may be secured to the lower leg by attached straps (not shown) or with tape to hold the leg bar 18 in its desired position along the outside of the leg.

As with the upper bar, the lower portion 36 of the lower bar is offset laterally from the upper portion 34 by a dog-leg intermediate portion 35, for a purpose to be described below.

Figure 4:
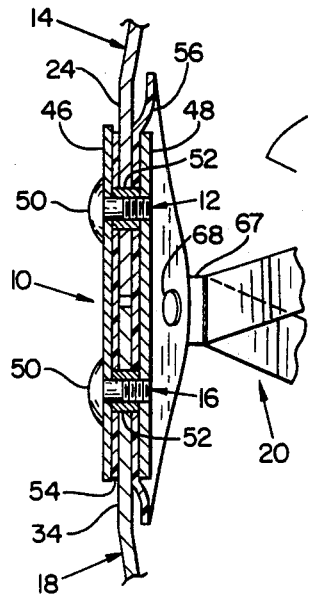
FIG. 4 is a cross-sectional view showing the construction of the shield plate assembly with its polycentric pivot joints.

The construction of the shield plate assembly 10 is shown best in FIG. 4. The assembly links the lower end 24 of upper leg bar 14 to the upper end 34 of lower bar 18 at their respective polycentric pivot joints 12, 16. The assembly includes adjacent ends 24, 34 of the upper and lower leg bars sandwiched between a pair of rigid rectangular clevis plates, including an outer clevis plate 46 and an inner clevis plate 48. Each plate, although relatively thin, is made of a strong, rigid lightweight material such as stainless steel. The two clevis plates are joined together by a pair of machine screws 50 extending through the outer clevis plate and apertures of the leg bar ends 24, 34, and threaded into threaded openings of the inner clevis plate 48. Screws 50 also pass through sleeve bushings 52 within the apertures of the leg bar ends. The bushings extend between the outer and inner clevis plates to serve as plate spacers and thereby enable free pivoting movement of the upper and lower leg bars about their respective sleeve bushings without binding between the clevis plates.

A thin, low friction plastic liner plate 54 similar in size and shape to the clevis plates lies between outer clevis plate 46 and the bar ends to minimize friction therebetween while still enabling the joints to be "tight," i.e., laterally rigid. Between the bar ends and inner clevis plate 48, a low-friction plastic knee plate 56 serves a similar function. However, referring to FIGS. 1 and 2, the knee plate is larger in area than the clevis plates, extending forwardly and rearwardly therefrom to form a rounded rear extension 58 and a pair of rounded forward ear portions 59. These portions are somewhat flexible.

Figure 2:
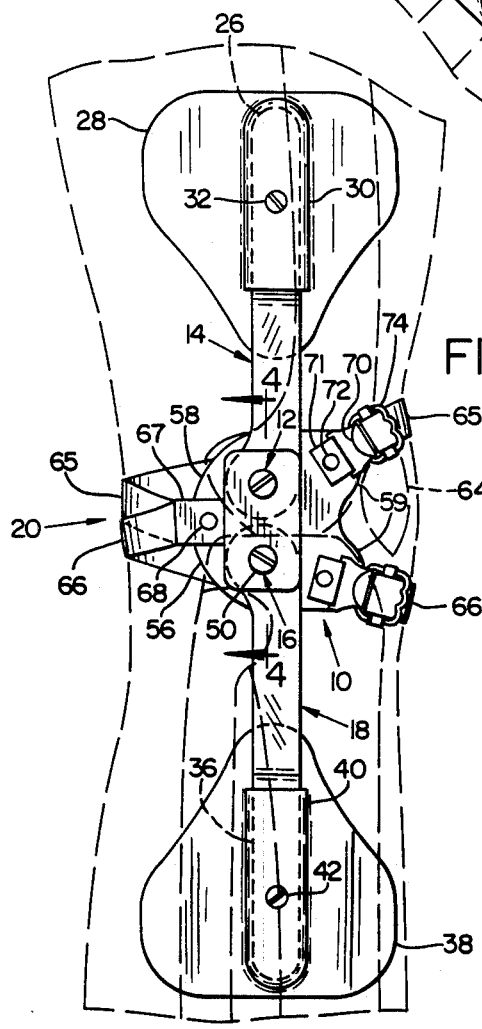
FIG. 2 is a second side view similar to FIG. 1 but showing the position of the knee brace on an extended leg.

As shown in FIGS. 1 and 2, the adjacent ends of the upper and lower leg bars in the resulting polycentric clevis joints are spaced slightly from one another and therefore fully pivotable independently of one another. Yet the adjacent ends are closely spaced apart, and thus the shield plate assembly can remain in a protective position at the knee in all positions of leg flexion. As best seen in FIG. 3, the axes of the upper and lower pivots 12, 16 are spaced substantially the same distance apart as the lateral centers of the lower outer condyle 60 of the femur and upper outer condyle 61 of the tibia, which maintain this separation throughout the knee joint's range of motion. Axis 62a of the upper leg bar is thus in substantial alignment with the corresponding axis 62b of the femur when the shield assembly 10 is positioned opposite the knee joint. Similarly, axis 63a of the bar is substantially aligned with the corresponding axis 63b of the tibia. The laterally rigid clevis joints 12, 16 thus always overlie the condyles of the femur and tibia as the leg flexes and extends.

Referring to FIG. 2, The knee plate 56 is shaped to receive the knee cap 64 between the ears 59 to position the shield plate assembly 10 over the knee joint. The assembly is held there throughout the knee joint's full range of motion by the strapping system 20 comprising a pair of elastic straps 65, 66 secured at a common position on the rear extension 58 of the knee plate by a section of nonelastic webbing 67 and a rivet 68. Buckle hooks 70 are attached one to each ear 56 by webbing 71 and rivets 72. Slide friction buckles 74 carried by straps 65, 66 attach the straps to buckle hooks 70. Thereafter, the free ends of the straps are pulled to adjust the straps for length. To hold the plate and assembly in position over the outside of the knee joint, the straps are stretched to encircle the back of the knee joint and straddle the knee cap 64 as shown in FIGS. 1—3.

In mounting the brace, the upper and lower leg bars are positioned along the outside of the leg as indicated in FIGS. 2 and 3. Optional latex straps or tape (not shown) may be wrapped across the plate 28, 38 and around the leg to assist in securing the brace to the leg, as indicated by phantom lines 76. The dog-leg portions 25, 35 of the leg bars 14, 18 allow the bars to follow the contour of the upper and lower leg inwardly toward the knee joint but bridge the knee joint with portions 24, 34 to hold the shield plate assembly away from the knee. This separation between the shield plate assembly and knee joint prevents the impact of a lateral blow to the assembly from being transmitted to the knee joint and transmitted instead away from the knee to a long length of the upper and lower leg. The strapping system 20 attached to the shield plate assembly is stretched to encircle the knee joint to retain the shield plate assembly in position throughout the full range of leg flexion.

In use, the brace does not restrict the mobility of the user. The double clevis joints accurately mimic the motion of the knee joint without hindering the pace, direction, or speed of the user. The single-side bracing prevents sideways movement of the knee joint otherwise caused by a sudden unnatural movement of the leg. The rigid shield assembly, more importantly, shields the joint from lateral blows as the leg flexes and extends. Because the shield assembly is separated from the knee joint, the force of the lateral blow is transmitted from the assembly through the rigid leg members and dissipated throughout a long length of the upper and lower leg.

Having illustrated and described the principles of our invention by reference to a preferred embodiment, it should be apparent to those persons skilled in the art that the preferred embodiment can be modified without departing from such principles. We claim as our invention all such modifications as come within the true spirit and scope of the following claims.

We claim:

1. A single-sided knee brace for athletic use comprising:
a rigid upper leg bar for extending along only one side of and securement to an upper leg;
a rigid lower leg bar for extending along only the same side of and securement to a lower leg;
a laterally rigid shield plate assembly linking adjacent ends of the upper and lower leg bars for independent movement about separate pivot axes;
securement means affixed to the shield plate assembly and encircling the knee joint for receiving the shield plate assembly laterally adjacent to a lateral side of the knee joint throughout the knee joint's range of motion,
said upper and lower leg bars being shaped such that when they are secured to their associated leg portions they position said shield plate assembly in laterally spaced relation to the adjacent knee joint, whereby lateral impact forces against said shield plate assembly are transmitted away from said knee joint to said upper and lower leg members.

2. The knee brace of claim 1 in which the shield plate assembly defines a pair of laterally rigid polycentric clevis joints forming upper and lower pivot axes attached to a knee plate.

3. The knee brace of claim 1 in which said securement means for securing the shield plate assembly laterally adjacent to the lateral side of the knee joint includes associated adjustable strap means attached to the knee plate which wrap entirely around the knee joint and connect to the knee plate.

4. The knee brace of claim 2 in which the upper and lower pivot axes of the polycentric joints are spaced substantially the same distance apart as the lateral centers of the adjacent outer condyles of the tibia and femur.

5. The knee brace of claim 4 in which the length of each leg member is greater than the distance between the pivot axes.

6. The knee brace of claim 1 in which said shield plate assembly further comprises:
a rigid outer plate;
a low-friction middle plate;
a rigid inner plate;
said knee plate; and
upper and lower pivot means extending through the outer plate, the middle plate, the lower end portion of the upper leg bar and the upper end portion of the lower leg bar, respectively, the knee plate and the inner plate to form a double clevis joint.

7. The knee brace of claim 6 in which the pivot means include:
a bearing sleeve separating the outer and inner plates but extending through the middle plate, the end portions of the leg bar and the knee plate; and
a fastening means extending through the sleeve and outer and inner plates for holding the joint together.

8. The knee brace of claim 1 including an upper side plate removably secured to an upper end of the upper leg bar for positioning the bar along the upper leg and a lower side plate removably secured to a lower end of the lower leg bar for positioning the bar along the lower leg.

9. A preventive knee brace comprising:
a rigid upper leg bar extending along the outside of an upper leg from the outer condyle of the femur toward the upper end of the femur;
a rigid lower leg bar extending along the outside of a lower leg from the outer condyle of the tibia toward the lower end of the tibia;
a shield plate assembly means defining polycentric clevis joints linking adjacent ends of the upper and lower leg bars to allow the upper and lower leg bars to pivot independently on separate pivot axes spaced substantially the same distance apart as the adjacent outer condyles of the femur and tibia;
said shield plate assembly including a knee plate having attached strap means for encircling the knee joint, the knee plate affixed to the double clevis joint for positioning the double clevis joint laterally adjacent to but not in contact with the lateral side of the knee joint so that an upper pivot means remains opposite the outer condyle of the femur and a lower pivot means remains opposite the outer condyle of the tibia throughout the knee joint's range of motion,
the upper and lower bars when secured to their associated leg portions positioning the polycentric pivot means in laterally spaced relation to the adjacent knee joint, whereby lateral impact forces against the polycentric pivot means are transmitted to the upper and lower leg bars away from the knee joint.

10. The knee brace of claim 9 in which the upper leg bar extends at least halfway up the length of the femur and the lower leg bar extends at least halfway down the length of the tibia.

11. A single-sided preventive knee brace for athletic use comprising:
a rigid upper leg bar for extension along the outside of a thigh from the knee of a user,
a rigid lower leg bar for extension along the outside of the lower leg from the knee of a user,
a rigid clevis plate means for overlying the outside of the knee joint of a user and interconnecting adjacent ends of said upper and lower leg bars for independent movement about polycentric parallel pivot axes extending through said plate means,
securing means for adjustably positioning said clevis plate means at the outside of the knee joint by encircling the joint above and below the knee cap.

12. A knee brace according to claim 11 wherein said clevis plate means comprises an outer rigid clevis plate overlying the outside of said adjacent ends, an inner rigid clevis plate overlying the inside of said adjacent ends, a semirigid low-friction knee plate extending between said inner clevis plate and the inside of said adjacent ends and extending forwardly and rearwardly beyond said clevis plates, a pair of sleeve bearings pivotally connecting said adjacent ends to said clevis plates, and fastening means extending through said clevis plates and knee plate and said sleeve bearings to interconnect said clevis plates with said adjacent ends and knee plate therebetween.

13. A knee brace according to claim 12 wherein said fastening means comprise a pair of threaded fasteners.

14. A knee brace according to claim 12 including a low-friction plastic liner interposed between said outer plate and said adjacent ends.

15. A knee brace according to claim 12 wherein said securing means includes a pair of hook means attached to a forward extension of said knee plate in longitudinally spaced-apart relationship to one another and a pair of straps attached at one set of ends thereof to a rearward extension of said knee plate at a common position thereon and having slide friction buckle means at the other set of ends thereof for attachment to said pair of hook means.

16. A knee brace according to claim 12 including a semirigid thigh plate at the upper free end of said upper leg bar and a semirigid calf plate at the lower free end of said lower leg bar, each of said thigh and calf plates including a sleeve on the rear surface thereof for slidably receiving its respective leg bar, and threaded fastener means for detachably securing said leg bar within said sleeve.

* * * * *